(12) United States Patent
Counter et al.

(10) Patent No.: US 8,771,982 B2
(45) Date of Patent: Jul. 8, 2014

(54) CHIMERIC MOLECULE AND NUCLEIC ACID ENCODING SAME

(75) Inventors: Christopher M. Counter, Durham, NC (US); Blaine N. Armbruster, Durham, NC (US)

(73) Assignee: Duke University, Durham, NC (US)

(*) Notice: Subject to any disclaimer, the term of this patent is extended or adjusted under 35 U.S.C. 154(b) by 2143 days.

(21) Appl. No.: 10/554,295

(22) PCT Filed: Apr. 30, 2004

(86) PCT No.: PCT/US2004/013799
§ 371 (c)(1),
(2), (4) Date: Aug. 15, 2006

(87) PCT Pub. No.: WO2004/099385
PCT Pub. Date: Nov. 18, 2004

(65) Prior Publication Data
US 2007/0020722 A1  Jan. 25, 2007

Related U.S. Application Data

(60) Provisional application No. 60/466,427, filed on Apr. 30, 2003.

(51) Int. Cl.
*C12P 21/06* (2006.01)
*C12N 9/00* (2006.01)
*C12N 9/22* (2006.01)
*C12N 1/20* (2006.01)
*C12N 15/00* (2006.01)
*C07H 21/04* (2006.01)

(52) U.S. Cl.
USPC ...... 435/69.1; 435/183; 435/199; 435/252.3; 435/320.1; 536/23.2

(58) Field of Classification Search
None
See application file for complete search history.

(56) References Cited

U.S. PATENT DOCUMENTS

| 5,770,422 | A | 6/1998 | Collins |
| 5,917,025 | A | 6/1999 | Collins |
| 6,093,809 | A | 7/2000 | Cech et al. |
| 6,166,178 | A | 12/2000 | Cech et al. |
| 6,261,836 | B1 | 7/2001 | Cech et al. |
| 6,309,867 | B1 | 10/2001 | Cech et al. |
| 6,337,200 | B1 | 1/2002 | Morin |
| 2002/0137703 | A1 | 9/2002 | Baumann et al. |

OTHER PUBLICATIONS

Evans et al. Science. Oct. 1, 1999;286(5437):117-20.*
Chica et al. Curr Opin Biotechnol. Aug. 2005;16(4):378-84.*
Sen et al. Appl Biochem Biotechnol. Dec. 2007;143(3):212-23.*
Evans et al, "EST 1 and Cdc13 as Comediators of Telomerase Access", Science 286:117-120 (1999).
Baumann et al, "Pot1, the Putative Telomere End-Binding Protein in Fission Yeast and Humans", Science 292:1171-1175 (2001).
Armbruster et al, "Putative-Telomere-Recruiting Domain in the Catalytic Subunit of Human Telomerase", Mol. Cell. Biol. 23(9):3237-3246 (2003).
Colgin et al, "Human POT1 Facilitates Telomere Elongation by Telomerase", Current Biol. 13:942-946 (2003).
Loayza et al, "POT1 as a terminal transducer of TRF1 telomere length control", Nature 423:1013-1018 (2003).
Kaminker et al, "TANK2, a New TRF1-associated Poly(ADP-ribose) Polymerase, Causes Rapid Induction of Cell Death upon Overexpression", The Journal of Biological Chemistry 276(38):35891-35899 (2001).
Armbruster et al, "Putative Telomere-Recruiting Domain in the Catalytic Subunit of Human Telomerase", Molecular and Cellular Biology 23(9):3237-3246 (2003).
Hsu et al, "Ku is associated with the telomere in mammals", PNAS 96(22):12454-12458 (1999).
Chong et al, "A Human Telomeric Protein", Science 270:1663-1668 (1995).
Smith et al, "Tankyrase, a Poly(ADP-Ribose) Polymerase at Human Telomeres", Science 282:1484-1487 (1998).
Zhou and Lu, "The Pin2/TRF1-Interacting Protein PinX1 Is a Potent Telomerase Inhibitor", Cell 107(3):347-359 (2001).
Li et al, "Identification of Human Rap1: Implications for Telomere Evolution", Cell 101(5):471-483 (2000).
Kim et al, "TIN2, a new regulator of telomere length in human cells", Nature Genetics 23:405-412 (1999).
Broccoli et al, "Human telomeres contain two distinct Myb-related proteins, TRF1 and TRF2", Nature Genetics 17:231-235 (1997).
Bryan et al, "Telomerase reverse transcriptase genes identified in *Tetrahymena thermophila* and *Oxytricha trifallax*", Pro Natl. Acad. Sci. USA 95:8470-8484 (1998).
Nakamura et al, "Telomerase Catalytic Subunit Homologs from Fission Yeast and Human", Science 277:955-959 (1997).

* cited by examiner

*Primary Examiner* — Christian Fronda
(74) *Attorney, Agent, or Firm* — Nixon & Vanderhye P.C.

(57) ABSTRACT

The present invention relates, in general, to telomeres, and, in particular, to a method or effecting telomere elongation in mammalian cells. The invention further relates to a protein suitable for use in such a method and to nucleic acid sequences encoding same.

14 Claims, 4 Drawing Sheets

```
TGGCTTTGCATCTTTGACGTTTGAGGGAACTTTGGGAGCCCCTATCATACCTCGCACTTCAAGCAAGTATTTTAACTTCA
CTACTGAGGACCACAAAATGGTAGAAGCCTTACGTGTTTGGGCATCTACTCATATGTCACCGTCTTGGACATTACTAAAA
TTGTGTGATGTTCAGCCAATGCAGTATTTTGACCTGACTTGTCAGCTCTTGGGCAAAGCAGAAGTGGACGGAGCATCATT
TCTTCTAAAGGTATGGGATGGCACCAGGACACCATTTCCATCTTGGAGAGTCTTAATACAAGACCTTGTTCTTGAAGGTG
ATTTAAGTCACATCCATCGGCTACAAAATCTGACAATAGACATTTTAGTCTACGATAACCATGTTCATGTGGCAAGATCT
CTGAAGGTTGGAAGCTTTCTTAGAATCTATAGCCTTCATACCAAACTTCAATCAATGAATTCAGAGAATCAGACAATGTT
AAGTTTAGAGTTTCATCTTCATGGAGGTACCAGTTACGGTCGGGGAATCAGGGTCTTACCAGAAAGTAACTCTGATGTGG
ATCAACTGAAAAAGGATTTAGAATCTGCAAATTTGACAGCCAATCAGCATTCAGATGTTATCTGTCAATCAGAACCTGAC
GACAGCTTTCCAAGCTCTGGATCAGTATCATTATACGAGGTAGAAAGATGTCAACAGCTATCTGCTACAATACTTACAGA
TCATCAGTATTTGGAGAGGACACCACTATGTGCCATTTTGAAACAAAAAGCTCCTCAACAATACCGCATCCGAGCAAAAT
TGAGGTCATATAAGCCCAGAAGACTATTTCAGTCTGTTAAACTTCATTGCCCTAAATGTCATTTGCTGCAAGAAGTTCCA
CATGAGGGCGATTTGGATATAATTTTTCAGGATGGTGCAACTAAAACCCCAGATGTCAAGCTACAAAATACATCATTATA
TGATTCAAAAATCTGGACCACTAAAAATCAAAAAGGACGAAAAGTAGCAGTTCATTTTGTGAAAAATAATGGTATTCTCC
CGCTTTCAAATGAATGTCTACTTTTGATAGAAGGAGGTACACTCAGTGAAATTTGCAAACTCTCGAACAAGTTTAATAGT
GTAATTCCTGTGAGATCTGGCCACGAAGACCTGGAACTTTTGGACCTTTCAGCACCATTTCTTATACAAGGAACAATACA
TCACTATGGATGTAAACAGTGTTCTAGTTTGAGATCCATACAAAATCTAAATTCCCTGGTTGATAAAACATCGTGGATTC
CTTCTTCTGTGGCAGAAGCACTGGGTATTGTACCCCTCCAATATGTGTTTGTTATGACCTTTACACTTGATGATGGAACA
GGAGTACTAGAAGCCTATCTCATGGATTCTGACAAATTCTTCCAGATTCCAGCATCAGAAGTTCTGATGGATGATGACCT
TCAGAAAAGTGTGGATATGATCATGGATATGTTTTGTCCTCCAGGAATAAAAATTGATGCATATCCGTGGTTGGAATGCT
TCATCAAGTCATACAATGTCACAAATGGAACAGATAATCAAATTTGCTATCAGATTTTTGACACCACAGTTGCAGAAGAT
GTAATCGTACGTAgGAATTCTAGATCTatgGACTACAAAGACGATGACGACAAGatgCCGCGCGCTCCCCGCTGCCGAGC
CGTGCGCTCCCTGCTGCGCAGCCACTACCGCGAGGTGCTGCCGCTGGCCACGTTCGTGCGGCGCCTGGGGCCCCAGGGCT
GGCGGCTGGTGCAGCGCGGGGACCCGGCGGCTTTCCGCGCGCTGGTGGCCCAGTGCCTGGTGTGCGTGCCCTGGGACGCA
CGGCCGCCCCCGCCGCCCCTCCTTCCGCCAGGTGTCCTGCCTGAAGGAGCTGGTGGCCCGAGTGCTGCAGAGGCTGTG
CGAGCGCGGCgCgAAgAACGTGCTGGCCTTCGGCTTCGCGCTGCTGGACGGGGCCCGCGGGGGCCCCCCCGAgCCTTCA
CCACCAGCGTGCGCAGCTACCTGCCCAACACGGTGACCgACgCACTGCGGGGGAGCGGGGCGTGGGGGCTGCTGcTGCGC
CGCGTGGGCGACGACGTGCTGGTTCACCTGCTGGCACGCTGCGCGCTCTTTGTGCTGGTGGCTCCCAGCTGCGCCTACCA
GGTGTGCGGGCCGCCGCTGTACCAGCTCGGCGCTGCCACTCAGGCCCGGCCCCCGCCACACGCTAGTGGACCCCGAAGGC
GTCTGGGATGCGAACGGCCTGGAACCATAGCGTCAGGGAGGCCGGGGTCCCCCTGGGCCTGCCAGCCCCGGGTGCGAGG
AGGCGCGGGGGCAGTGCCAcCCGAAGTCTGCCGTTGCCCAAGAGGCCCAGGCGTGGCGCTGCCCCTGAGCCGGAGCGGAC
GCCCGTTGGGCAGGGGTCCTGGGCCCACCCGGGCAGGACGCGTGGACCGAGTGACCGTGGTTTCTGTGTGGTGTCACCTG
CCAGACCCGCCGAAGAAGCCACCTCTTTGGAGGGTGCGCTCTCTGGCACGCGCCACTCCCACCCATCCGTGGGCCGCCAG
CACCACGCGGGCCCCCCATCCACATCGCGGCCACCACGTCCCTGGGACACGCCTTGTCCCCCGGTGTACGCCGAGACCAA
GCACTTCCTCTACTCCTCAGGCGACAAGGAGCAGCTGCGGCCCTCCTTCCTACTCAGCTCTCTGAGGCCCAGCCTGACTG
GCGCTCGGAGGCTCGTGGAGACCATCTTTCTGGGTTCCAGGCCCTGGATGCCAGGGACTCACGACGCGGTTGCCCCGCCTG
CCCCAGCGCTACTGGCAAATACGGCCCCTGTTTCTGGAGCTGCTTGGGAACCACGCGCAGTGCCCCTACGGGTGCTCCT
CAAGACGCACTGCCCGCTGCGAGCTGCGGTCACCCCAGCAGCCGGTGTCTGTGCCCGGGAGAAGCCCCAGGGCTCTGTGG
CGGCCCCCGAGGAGGAGGACACAGACCCCGTCGCCTGGTGCAGCTGCTCCGCCAGCACAGCAGCCCCTGGCAGGTGTAC
GGCTTCGTGCGGGCCTGCCTGCGCCGGCTGGTGCCCCCAGGCCTCTGGGGCTCCAGGCACAACGAACGCCGCTTCCTCAG
GAACACCAAGAAGTTCATCTCCCTGGGGAAGCATGCCAAGCTCTCGCTGCAGGAGCTGACGTGGAAGATGAGCGTGCGGG
GCTGCGCTTGGCTGCGCAGGAGCCCAGGGGTTGGCTGTGTTCCGGCCGCAGAGCACCGTCTGCGTGAGGAGATCCTGGCC
AAGTTCCTGCACTGGCTGATGAGTGTGTACGTCGTCGAGCTGCTCAGGTCTTTCTTTTATGTCACGGAGACCACGTTTCA
AAAGAACAGGCTCTTTTTCTACCGGAAGAGTGTCTGGAGCAAGTTGCAAAGCATTGGAATCAGACAGCACTTGAAGAGGG
TGCAGCTGCGGGAGCTGTCGGAAGCAGAGGTCAGGCAGCATCGGGAAGCCAGGCCCGCCCTGCTGACGTCCAGACTCCGC
TTCATCCCCAAGCCTGACGGGCTGCGGCCGATTGTGAACATGGACTACGTCGTGGGAGCCAGAACGTTCCGCAGAGAAAA
GAGGGCCGAGCGTCTCACCTCGAGGGTGAAGGCACTGTTCAGCGTGCTCAACTACGAGCGGGCGCGGCGCCCCGGCCTCC
TGGGCGCCTCTGTGCTGGGCCTGGACGATATCCACAGGGCCTGGCGCACCTTCGTGCTGCGTGCGGGCCCAGGACCCG
CCGCCTGAGCTGTACTTTGTCAAGGTGGATGTGACGGGCGCGTACGACACCATCCCCCAgGACAGGCTCACGGAGGTCAT
CGCCAGCATCATCAAACCCCAGAACACGTACTGCGTGCGTCGGTATGCCGTGGTCCAGAAGGCCGCCCATGGGCACGTCC
GCAAGGCCTTCAAGAGCCACGTCTCTACCTTGACAGACCTCCAGCCGTACATGCGACAGTTCGTGGCTCACCTGCAGGAG
ACCAGCCCGCTGAGGGATGCCGTCGTCATCGAGCAGAGCTCCTCCCTGAATGAGGCCAGCAGTGGCCTCTTCGACGTCTT
CCTACGCTTCATGTGCCACCACGCCGTGCGCATCAGGGGCAAGTCCTACGTCCAGTGCCAGGGGATCCCGCAGGGCTCCA
TCCTCTCCACGCTGCTCTGCAGCCTGTGCTACGGCGACATGGAGAACAAGCTGTTTGCGGGGATTCGGCGGGACGGGCTG
CTCCTGCGTTTGGTGGATGATTTCTTGTTGGTGACACCTCACCTCACCCACGCGAAAACCTTCCTCAGGACCCTGGTCCG
AGGTGTCCCTGAGTATGGCTGCGTGGTGAACTTGCGGAAGACAGTGGTGAACTTCCCTGTAGAAGACGAGGCCCTGGGTG
GCACGGCTTTTGTTCAGATGCCGGCCCACGGCCTATTCCCCTGGTGCGGCCTGCTGCTGGATACCCGGACCCTGGAGGTG
CAGAGCGACTACTCCAGCTATGCCCGGACCTCCATCAGAGCCAGTCTCACCTTCAACCGCGGCTTCAAGGCTGGGAGGAA
CATGCGTCGCAAACTCTTTGGGGTCTTGCGGCTGAAGTGTCACAGCCTGTTTCTGGATTTGCAGGTGAACAGCCTCCAGA
CGGTGTGCACCAACATCTACAAGATCCTCCTGCTGCAGGCGTACAGGTTTCACGCATGTGTGCTGCAGCTCCCATTTCAT
CAGCAAGTTTGGAAGAACCCCACATTTTTCCTGCGCGTCATCTCTGACACGGCCTCCCTCTGCTACTCCATCCTGAAAGC
CAAGAACGCAGGGATGTCGCTGGGGGCCAAGGGCGCCGCCGGCCCTCTGCCCTCCGAGGCCGTGCAGTGGCTGTGCCACC
AAGCATTCCTGCTCAAGCTGACTCGACACCGTGTCACCTACGTGCCACTCCTGGGGTCACTCAGGACAGCCCAGACGCAG
CTGAGTCGGAAGCTCCCGGGGACGACGCTGACTGCCCTGGAGGCCGCAGCCAACCCGGCACTGCCCTCAGACTTCAAGAC
CATCCTGGACTGAGTCGAC
```

Figure 1. Nucleotide sequence of encoded hPot1-hTERT fusion protein.

Figure 2. hTERT proteins retain telomerase activity when fused to hPot1. (A) Lysates from HA5 cell expressing the described constructs were immunoblotted with anti-flag antibodies to detect ectopic hTERT containing proteins. Actin serves as a loading control. (B) Lysates were assayed for *in vitro* telomerase activity. The internal standard (IS) served as a positive control for PCR amplification.

Figure 3. The hPot1-hTERT chimeric proteins elongate telomeres. Restriction enzyme digested genomic DNA isolated from late passage HA5 cells expressing hTERT, hPot-hTERT or hPot1-hTERT$_{+128}$ and from HA5 cells were hybridized with a telomeric probe to visualize telomere containing fragments. Left, molecular weight markers in kilo bases (Kb). Sample for hPot1-hTERT was underloaded (*).

Figure 4. HA5 cells expressing hPot1-hTERT fusion proteins immortalize. The lifespan in population doublings (pd) of HA5 cell lines infected with vectors expressing hPot1-hTERT (□), hPot1-hTERT+128 (○) or controls expressing vector alone (▲), hTERT (■) or hTERT+128 (●) is plotted against time in days.

SEQUENCE LISTING

<160> NUMBER OF SEQ ID NOS: 3

<210> SEQ ID NO 1
<211> LENGTH: 5379
<212> TYPE: DNA

```
<213> ORGANISM: Artificial Sequence
<220> FEATURE:
<223> OTHER INFORMATION: Description of Artificial Sequence:Probe

<400> SEQUENCE: 1
atggactaca aagacgatga cgacaagtct tggttccag caacaaatta tatatataca      60
cccctgaatc aacttaaggg tggtacaatt gtcaatgtct atggtgttgt gaagttcttt    120
aagcccccat atctaagcaa aggaactgat tattgctcag ttgtaactat tgtggaccag    180
acaaatgtaa aactaacttg cctgctcttt agtggaaact atgaagccct tccaataatt    240
tataaaaatg gagatattgt tcgctttcac aggctgaaga ttcaagtata taaaaaggag    300
actcagggta tcaccagctc tggctttgca tctttgacgt ttgagggaac tttgggagcc    360
cctatcatac ctcgcacttc aagcaagtat tttaacttca ctactgagga ccacaaaatg    420
gtagaagcct tacgtgtttg ggcatctact catatgtcac cgtcttggac attactaaaa    480
ttgtgtgatg ttcagccaat gcagtatttt gacctgactt gtcagctctt gggcaaagca    540
gaagtggacg gagcatcatt tcttctaaag gtatgggatg caccaggac accatttcca     600
tcttggagag tcttaataca agaccttgtt cttgaaggtg atttaagtca catccatcgg    660
ctacaaaatc tgacaataga catttttagtc tacgataacc atgttcatgt ggcaagatct   720
ctgaaggttg aagctttct tagaatctat agccttcata ccaaacttca atcaatgaat    780
tcagagaatc agacaatgtt aagtttagag tttcatcttc atggaggtac cagttacggt    840
cggggaatca gggtcttacc agaaagtaac tctgatgtgg atcaactgaa aaaggattta    900
gaatctgcaa atttgacagc caatcagcat tcagatgtta tctgtcaatc agaacctgac    960
gacagctttc caagctctgg atcagtatca ttatacgagg tagaaagatg tcaacagcta   1020
tctgctacaa tacttacaga tcatcagtat ttggagagga caccactatg tgccattttg   1080
aaacaaaaag ctcctcaaca ataccgcatc cgagcaaaat tgaggtcata taagcccaga   1140
agactatttc agtctgttaa acttcattgc cctaaatgtc atttgctgca agaagttcca   1200
catgagggcg atttggatat aattttttcag gatggtgcaa ctaaaacccc agatgtcaag   1260
ctacaaaata tcatcattata tgattcaaaa atctggacca ctaaaaatca aaaggacga   1320
aaagtagcag ttcattttgt gaaaaataat ggtattctcc cgctttcaaa tgaatgtcta   1380
cttttgatag aaggaggtac actcagtgaa atttgcaaac tctcgaacaa gtttaatagt   1440
gtaattcctg tgagatctgg ccacgaagac ctggaacttt tggacctttc agcaccattt   1500
cttatacaag gaacaataca tcactatgga tgtaaacagt gttctagttt gagatccata   1560
caaaatctaa attccctggt tgataaaaca tcgtggattc cttcttctgt ggcagaagca   1620
ctgggtattg tacccctcca atatgtgttt gttatgacct ttacacttga tgatggaaca   1680
ggagtactag aagcctatct catggattct gacaaattct tccagattcc agcatcagaa   1740
gttctgatgg atgatgacct tcagaaaagt gtggatatga tcatggatat gttttgtcct   1800
ccaggaataa aaattgatgc atatccgtgg ttggaatgct tcatcaagtc atacaatgtc   1860
acaaatggaa cagataatca aatttgctat cagattttg acaccacagt tgcagaagat    1920
gtaatcgtac gtaggaattc tagatctatg gactacaaag acgatgacga caagatgccg   1980
cgcgctcccc gctgccgagc cgtgcgctcc ctgctgcgca gccactaccg cgaggtgctg   2040
ccgctggcca cgttcgtgcg gcgcctgggg cccagggct ggcggctggt gcagcgcggg   2100
gacccggcgc ctttccgcgc gctggtggcc cagtgcctgg tgtgcgtgcc ctgggacgca   2160
cggccgcccc ccgccgcccc ctccttccgc caggtgtcct gcctgaagga gctggtggcc   2220
```

```
cgagtgctgc agaggctgtg cgagcgcggc gcgaagaacg tgctggcctt cggcttcgcg    2280
ctgctggacg gggcccgcgg gggcccccc gaggccttca ccaccagcgt gcgcagctac    2340
ctgcccaaca cggtgaccga cgcactgcgg gggagcgggg cgtgggggct gctgctgcgc    2400
cgcgtgggcg acgacgtgct ggttcacctg ctggcacgct gcgcgctctt tgtgctggtg    2460
gctcccagct gcgcctacca ggtgtgcggg ccgccgctgt accagctcgg cgctgccact    2520
caggcccggc ccccgccaca cgctagtgga ccccgaaggc gtctgggatg cgaacgggcc    2580
tggaaccata gcgtcaggga ggccggggtc ccctgggcc tgccagcccc gggtgcgagg    2640
aggcgcgggg gcagtgccac ccgaagtctg ccgttgccca agaggccag gcgtggcgct    2700 gcccctgagc cggagcggac gcccgttggg caggggtcct gggcccaccc gggcaggacg    2760
cgtggaccga gtgaccgtgg tttctgtgtg gtgtcacctg ccagacccgc cgaagaagcc    2820
acctctttgg agggtgcgct ctctggcacg cgccactccc acccatccgt gggccgccag    2880
caccacgcgg gcccccatc cacatcgcgg ccaccacgtc cctgggacac gccttgtccc    2940
ccggtgtacg ccgagaccaa gcacttcctc tactcctcag gcgacaagga gcagctgcgg    3000
ccctccttcc tactcagctc tctgaggccc agcctgactg gcgctcggag gctcgtggag    3060
accatctttc tggggttccag gccctggatg ccagggactc cccgcaggtt gccccgcctg    3120
ccccagcgct actggcaaat gcggcccctg tttctggagc tgcttgggaa ccacgcgcag    3180 tgccctacg gggtgctcct caagacgcac tgcccgctgc gagctgcggt caccccagca    3240
gccggtgtct gtgcccggga gaagccccag ggctctgtgg cggcccccga ggaggaggac    3300
acagaccccc gtcgcctggt gcagctgctc cgccagcaca gcagcccctg gcaggtgtac    3360
ggcttcgtgc gggcctgcct gcgccggctg gtgcccccag gcctctgggg ctccaggcac    3420
aacgaacgcc gcttcctcag gaacaccaag aagttcatct ccctggggaa gcatgccaag    3480
ctctcgctgc aggagctgac gtggaagatg agcgtgcggg gctgcgcttg gctgcgcagg    3540
agcccagggg ttggctgtgt tccggccgca gagcaccgtc tgcgtgagga gatcctggcc    3600
aagttcctgc actggctgat gagtgtgtac gtcgtcgagc tgctcaggtc tttcttttat    3660
gtcacggaga ccacgtttca aaagaacagg ctctttttct accggaagag tgtctggagc    3720
aagttgcaaa gcattggaat cagacagcac ttgaagaggg tgcagctgcg ggagctgtcg    3780
gaagcagagg tcaggcagca tcgggaagcc aggcccgccc tgctgacgtc cagactccgc    3840
ttcatcccca gcctgacgg gctgcggccg attgtgaaca tggactacgt cgtgggagcc    3900
agaacgttcc gcagagaaaa gagggccgag cgtctcacct cgagggtgaa ggcactgttc    3960
agcgtgctca actacgagcg ggcgcggcgc cccggcctcc tgggcgcctc tgtgctgggc    4020
ctggacgata tccacagggc ctggcgcacc ttcgtgctgc gtgtgcgggc ccaggacccg    4080
ccgcctgagc tgtactttgt caaggtggat gtgacgggcg cgtacgacac catccccag    4140 gacaggctca cggaggtcat cgccagcatc atcaaacccc agaacacgta ctgcgtgcgt    4200
cggtatgccg tggtccagaa ggccgcccat gggcacgtcc gcaaggcctt caagagccac    4260
gtctctacct tgacagacct ccagccgtac atgcgacagt tcgtggctca cctgcaggag    4320
accagcccgc tgagggatgc cgtcgtcatc gagcagagct cctccctgaa tgaggccagc    4380
agtggcctct tcgacgtctt cctacgcttc atgtgccacc acgccgtgcg catcagggc    4440 aagtcctacg tccagtgcca ggggatcccg caggggtccca tcctctccac gctgctctgc    4500
agcctgtgct acggcgacat ggagaacaag ctgtttgcgg ggattcggcg ggacgggctg    4560
```

```
ctcctgcgtt tggtggatga tttcttgttg gtgacacctc acctcaccca cgcgaaaacc    4620
ttcctcagga ccctggtccg aggtgtccct gagtatggct gcgtggtgaa cttgcggaag    4680
acagtggtga acttccctgt agaagacgag gccctgggtg gcacggcttt tgttcagatg    4740
ccggcccacg gcctattccc ctggtgcggc ctgctgctgg atacccggac cctggaggtg    4800
cagagcgact actccagcta tgcccggacc tccatcagag ccagtctcac cttcaaccgc    4860
ggcttcaagg ctgggaggaa catgcgtcgc aaactctttg gggtcttgcg gctgaagtgt    4920
cacagcctgt ttctggattt gcaggtgaac agcctccaga cggtgtgcac caacatctac    4980
aagatcctcc tgctgcaggc gtacaggttt cacgcatgtg tgctgcagct cccatttcat    5040
cagcaagttt ggaagaaccc cacattttc ctgcgcgtca tctctgacac ggcctccctc    5100
tgctactcca tcctgaaagc caagaacgca gggatgtcgc tggggggccaa gggcgccgcc    5160 ggccctctgc cctccgaggc cgtgcagtgg ctgtgccacc aagcattcct gctcaagctg    5220
actcgacacc gtgtcaccta cgtgccactc ctggggtcac tcaggacagc ccagacgcag    5280
ctgagtcgga agctcccggg gacgacgctg actgccctgg aggccgcagc caacccggca    5340
ctgccctcag acttcaagac catcctggac tgagtcgac                           5379

<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence:Primer

<400> SEQUENCE: 2
cgggatccta cgtagctagc atggactaca aagacgatga cgacaagtct ttggttccag    60
caacaaat                                                             68

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence:Primer

<400> SEQUENCE: 3
cgacgtcgac taaatacgta cgattacatc ttctgcaact gtg                      43
```

CHIMERIC MOLECULE AND NUCLEIC ACID ENCODING SAME

This application is the U.S. national phase of international application PCT/US2004/013799 filed on 30 Apr. 2004, which designated the US and claims priority from U.S. Provisional Application No. 60/466,427 filed 30 Apr. 2003. The entire contents of these applications are incorporated herein by reference.

TECHNICAL FIELD

The present invention relates, in general, to telomeres, and, in particular, to a method or effecting telomere elongation in mammalian cells. The invention further relates to a protein suitable for use in such a method and to nucleic acid sequences encoding same.

BACKGROUND

Loss of telomeres limits the lifespan of human cells and thus greatly impedes the ability of mammalian tissues to be manipulated for the purposes of, for example, tissue engineering. It has been demonstrated that ectopic expression of hTERT (the catalytic protein subunit of human telomerase reverse transcriptase) in human cells can arrest telomere shortening and immortalize cells. However, sustained expression of hTERT can promote tumor growth. Thus, use in humans of cells manipulated by sustained expression of hTERT raises concerns relating to the induction of tumorigenic growth of manipulated cells. This problem could be overcome by transient expression of hTERT, however, transient expression may not result in sufficient elongation of telomeres to provide for extended culturing.

The present invention provides a safe and efficient method of elongating telomere length of cells, e.g., cultured human cells. The method makes possible, for example, a variety of tissue engineering techniques.

SUMMARY OF THE INVENTION

In general, the present invention relates to telomeres. More specifically, the invention relates to a method or effecting telomere elongation in mammalian cells. In addition, the invention relates to a protein suitable for use in such a method and to nucleic acid sequences encoding same.

Objects and advantages of the present invention will be clear from the description that follows.

BRIEF DESCRIPTION OF THE DRAWINGS

FIG. 1. Nucleotide sequence of encoded hPot1-hTERT fusion protein (SEQ ID NO:1).

FIGS. 2A and 2B. hTERT proteins retain telomerase activity when fused to hPot1. (FIG. 1A) Lysates from HA5 cell expressing the described constructs were immunoblotted with anti-flag antibodies to detect ectopic hTERT containing proteins. Actin serves a loading control. (FIG. 1B) Lysates were assayed for in vitro telomerase activity. The internal standard (IS) served as a positive control for PCR amplification.

DETAILED DESCRIPTION OF THE INVENTION hTERT is known to elongate telomeres when introduced into human cells (Collins et al, Oncogene 21:564-579 (2002)). However, this enzyme cannot extend telomeric DNA extensively in many human cells. The present invention provides a chimeric molecule, and a nucleic acid sequence encoding same, that can greatly elongate telomeres. The chimeric molecule comprises a protein having telomerase catalytic activity fused to a telomere binding protein.

Advantageously, the protein having telomerase catalytic activity is the catalytic protein subunit of telomerase reverse transcriptase, for example, mammalian telomerase reverse transcriptase, e.g., human telomerase reverse transcriptase (hTERT) (GENBANK DNA accession #AH007699; GENBANK protein sequence accession #BAA74724), or functional portion or variant thereof. Examples of such portions/variants are given in U.S. Pat. Nos. 5,770,422, 5,917,025, 6,093,809, 6,166,178, 6,261,836, 6,309,867, and 6,337,200.

The telomere binding protein is, advantageously, Pot1 (e.g., hPot1), or functional portion or variant thereof (see U.S. Application Ser. No. 20020137703), or other telomere binding or telomere associated protein such as TRF1 (Chong et al, Science 270:1663-1667 (1995)), TRF2 (Broccoli et al, Nat. Genet. 17:231-235 (1997)), PinX1 (Zhou et al, Cell 107:347-359 (2001)), Rap1 (Li et al, Cell 101:471-483 (2000)), Tin2 (Kim et al, Nat. Genet. 23:405-412 (1999)), Tankyrase (Smith et al, Science 282:1484-1487 (1998)), TANK2 (Kaminker et al, J. Biol. Chem. 276:35891-35899 (2001)) or Ku70/80 (Hsu et al, Proc. Natl. Acad. Sci. USA 96:12454-12458 (1999)), or functional portion or variant thereof (see also Armbruster et al, Mol. Cell. Biol. 23:3237-3246 (2003)). The binding protein can be present in the chimeric molecule N-terminal or C-terminal to the protein having telomerase catalytic activity, however, N-terminal is preferred. The two components of the chimeric molecule can be linked directly or indirectly, e.g., via a spacer polypeptide or peptide or by homo- or heterodimerization via fusion to other proteins.

The invention also relates to nucleic acid sequences encoding the above-described chimeric molecule, the sequence given in FIG. 1 (SEQ ID NO:1) being an example. Advantageously, the encoding sequence is present in an expression construct, typically in operable linkage with a promoter. Preferred promoters include high transcription rate promoters, such as any viral promoter (e.g., SV40) or a tetracycline-inducible promoter. (See also U.S. application Ser. No. 10/388,588, incorporated herein by reference, and particularly disclosure therein relating to construct components).

Any of the above protein/nucleic acid sequences can be prepared chemically or recombinantly using standard techniques.

The nucleic acids of the invention can be introduced into any of a variety of cell types, for example, to provide constituent cells of required tissues. The introduction can be effected using any of a variety of approaches, which can vary with the nature of the construct employed and cell type targeted. For example, viral vectors can be used to introduce the nucleic acids of the invention into target cells (e.g., retroviral vectors, adeno-associated viral vectors, lentiviral vectors and adenoviral vectors). Non-viral delivery methods can also be used to introduce constructs containing the nucleic acids of the invention into target cells. For example, liposome-encapsulated constructs can be used as can polymer-encapsulated constructs, receptor-mediated transfer of such encapsulated constructs, polymer-complexed constructs, constructs incorporated by electroporation, constructs incorporated by calcium phosphate precipitation, and naked constructs (Templeton et al, Gene Therapy: therapeutic mechanisms and strategies, New York (2000), Pasi, British Journal of Haematology 115:744-757 (2001)). (See also U.S. application Ser. No. 10/388,588.)

Any of a variety of cell types can be modified to include the nucleic acids of the invention (examples of such cells include stem/progenitor cells, epithelial cells, fibroblasts, muscle cells, nervous system cells, keratinocytes, etc.). Introduction of the nucleic acids of the invention can be effected to immortalize cells, cells so immortalized being useful, for example, in tissue engineering (e.g., to produce vascular grafts—see U.S. application Ser. No. 10/388,588) (Counter et al, Lancet 361:1345-1346 (2003), McKee et al, EMBO Reports, in press (2003)), bone marrow transplants (Shi et al, Nat. Biotechnol. 20:587-591 (2002)). Immortalized cells can also be used in the treatment of diseases or conditions where there is a significant cell turnover (e.g., engraftment of burns or liver disease).

As noted above, hTERT is activated in cancer cells (Collins and Mitchell, Oncogene 21:564-579 (2002), Meyerson et al, Cell 90:785-795 (1997)) and is known to be a step in tumorigenesis (Collins and Mitchell, Oncogene 21:564-579 (2002), Hahn et al, Nature 400:464-468 (1999), Shay and Bacchetti, Eur. J. Cancer 33:787-791 (1997)), making constitutive expression of this potentially dangerous. Transient expression of hTERT has been argued as a means to overcome this limitation but the period of time that hTERT is expressed may not be sufficient to elongate telomeres enough for clinical applications or long term sustainability in the human body. However, transient expression of a nucleic acid sequence of the invention, and production of the encoded chimeric molecule, can be used for such applications.

Certain aspects of the invention can be described in greater detail in the non-limiting Example that follows.

EXAMPLE

Experimental Details

Constructs (FIG. 1)

A chimeric protein of hPot1 (accession number NM_015450) was engineered to contain a FLAG-epitope tag fused to the N-terminus of hTERT (accession number AF018167) previously engineered to contain a FLAG-epitope tag (Armbruster et al, Mol. Cell Biol. 21:7775-7786 (2001)). Specifically, hPot1 cDNA in the plasmid pQE30-hPot1 (gift of Dr. Tom Cech, Boulder Colo.) was PCR amplified with primers 5'-cgGGATCCTACGTAGCTAGCatgGACTACAAAGACGATGACGACAAGTCTTTGGTTCCAGCAACAAAT (SEQ ID NO:2) and 5'-cgacGTCGACtaaaTACGTAcGATTACATCTTCTGCAACTGTG (SEQ ID NO:3) to generate an N-terminal flag epitope tagged hPot1 lacking a terminating codon (flag-hPot1). The resultant product was subcloned into the BamHI/SalI sites of pBluescript SK− (Stratagene) and sequenced to verify that the sequence was correct. Flag-hPot1 was then excised from this plasmid with SnaBI and cloned into the same site in the retroviral construct pBabepuro-flag-hTERT (Armbruster et al, Mol. Cell Biol. 23:3237-3246 (2003)), generating pBabepuro-flag-hPot1-flag-hTERT. Similarly, the same Flag-hPot1 fragment was cloned into the SnaBI site of pBabepuro-flag-hTERT$_{+128}$ (Armbruster et al, Mol. Cell Biol. 23:3237-3246 (2003)), generating the plasmid pBabepuro-flag-hPot1-flag-hTERT$_{+128}$. Plasmids pBabepuro, pBabepuro-flag-hTERT$_{+128}$, and pBabepuro-flag-hTERT were previously described (Armbruster et al, Mol. Cell Biol. 23:3237-3246 (2003), Morgenstern and Land, Nucleic Acids Res. 18:1068 (1990)).

Figure 2:
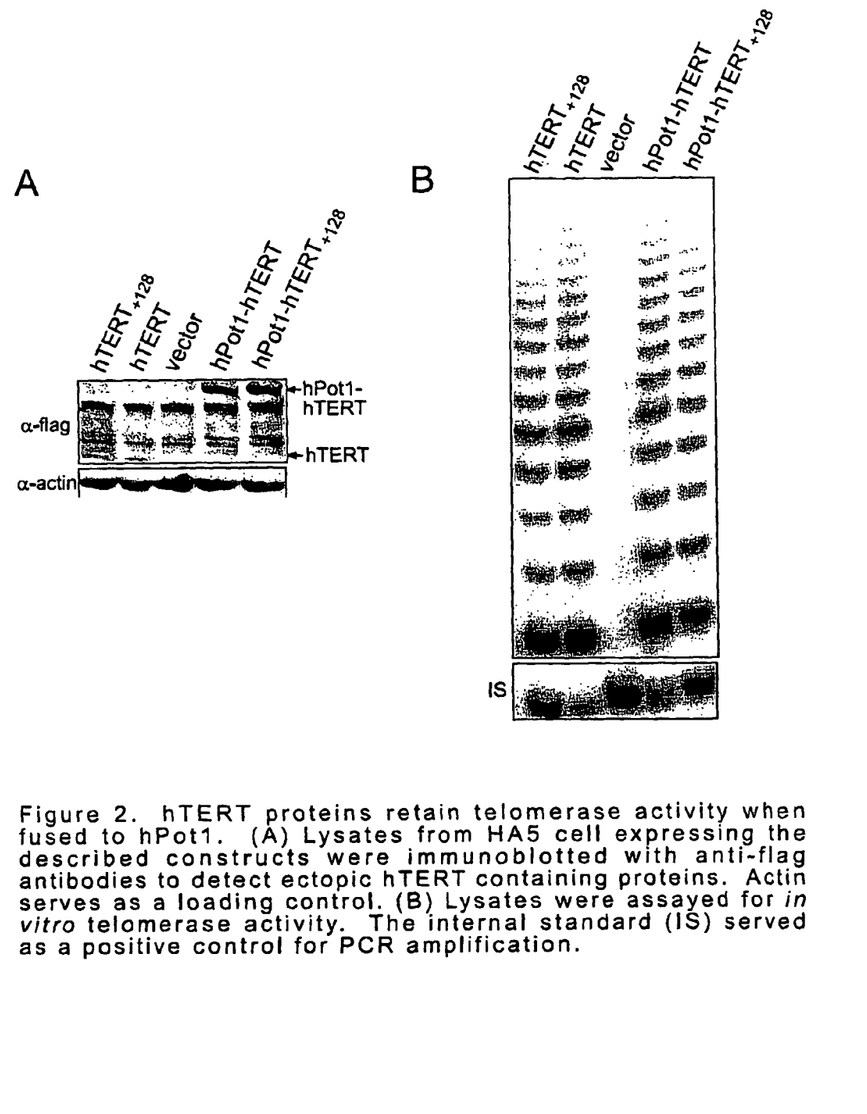
Figure 4:
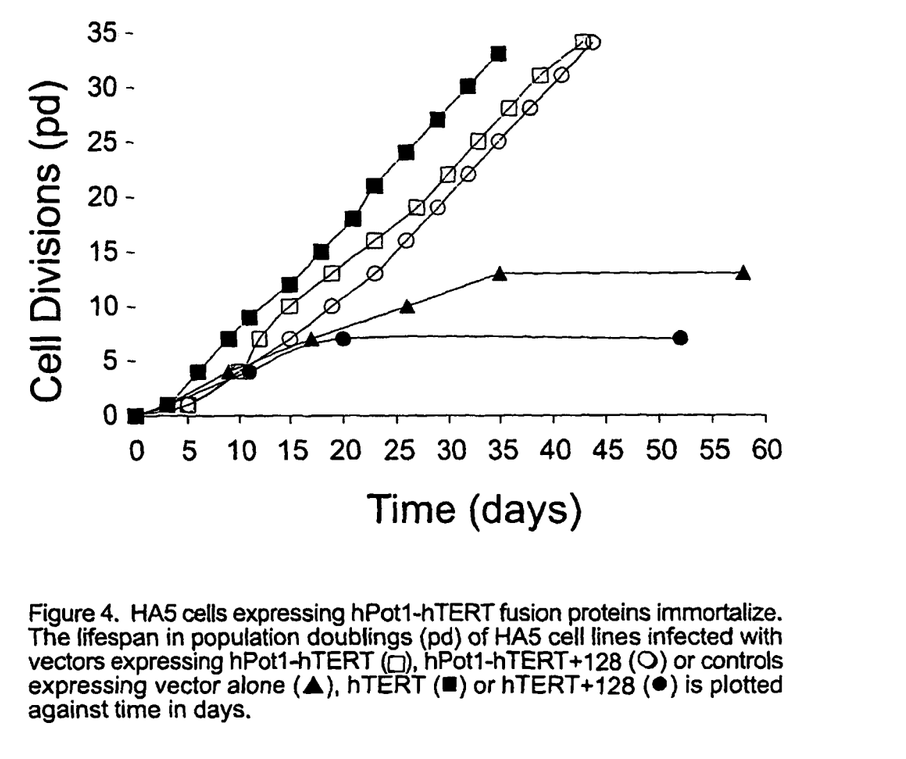
FIG. 4. HA5 cells expressing hPot-hTERT fusion proteins immortalize. The lifespan in population doublings (pd) of HA5 cell lines infected with vectors expressing hPot-hTERT (□), hPot-hTERT$_{+128}$ (○) or controls expressing vector alone (▲), hTERT (■) or hTERT$_{+128}$ (●) is plotted against time in days.

Cell Culture and Immortalization (FIGS. 2 and 4)

At late passage, cells of the SV40 early region transformed human embryonic kidney cell line HA5 (Stewart and Bacchetti, Virology 180:49-57 (1991)) were infected with amphotropic retrovirus derived from the constructs pBabepuro-flag-hPot1-flag-hTERT and pBabepuro-flag-hPot1-flag-hTERT$_{+128}$ or, as controls, pBabepuro, pBabepuro-flag-hTERT$_{+128}$, and pBabepuro-flag-hTERT using methods identical to those previously described (Armbruster et al, Mol. Cell Biol. 21:7775-7786 (2001)). Stably infected polyclonal populations were selected in media supplemented with 1.0 µg/ml puromycin (Sigma). Population doubling (PD) 0 was arbitrarily assigned to the first confluent plate under selection. The resultant five cell lines were continually passaged 1:8 under selection until either crisis or until the culture divided 2.5 times more than vector-control cell lines. Crisis was defined as the period when cultures failed to become confluent within 4 weeks and displayed massive cell death.

Protein Expression (FIG. 2)

150 µg of soluble lysate from the aforementioned five cell lines was separated by SDS-PAGE, and immunoblotted as previously described (Armbruster et al, Mol. Cell Biol. 23:3237-3246 (2003)) with the primary mouse monoclonal antibodies anti-FLAG M2 (Sigma) and anti-actin C-2 (Santa Cruz Biotechnology Inc.) to detect flag-hTERT or acting respectively, followed by incubation with the goat anti-mouse IgG-HRP (81-6520) (Zymed Laboratories Inc.). Proteins were then detected with ECL reagent following the manufacturer's protocol (Amersham Pharmacia Biotech).

Detection of In Vitro Telomerase Activity (FIG. 2)

0.2 µg of lysates prepared from the aforementioned five cell lines at early passage were assayed for telomerase activity using the telomeric repeat amplification protocol (Kim and Wu, Nucleic Acids Res. 25:2595-2597 (1997)). Reaction products were resolved on 10% polyacrylamide gels, dried and exposed to a phosphorimager screen to visualize enzyme activity, as previously described (Kim and Wu, Nucleic Acids Res. 25:2595-2597 (1997)).

Figure 3:
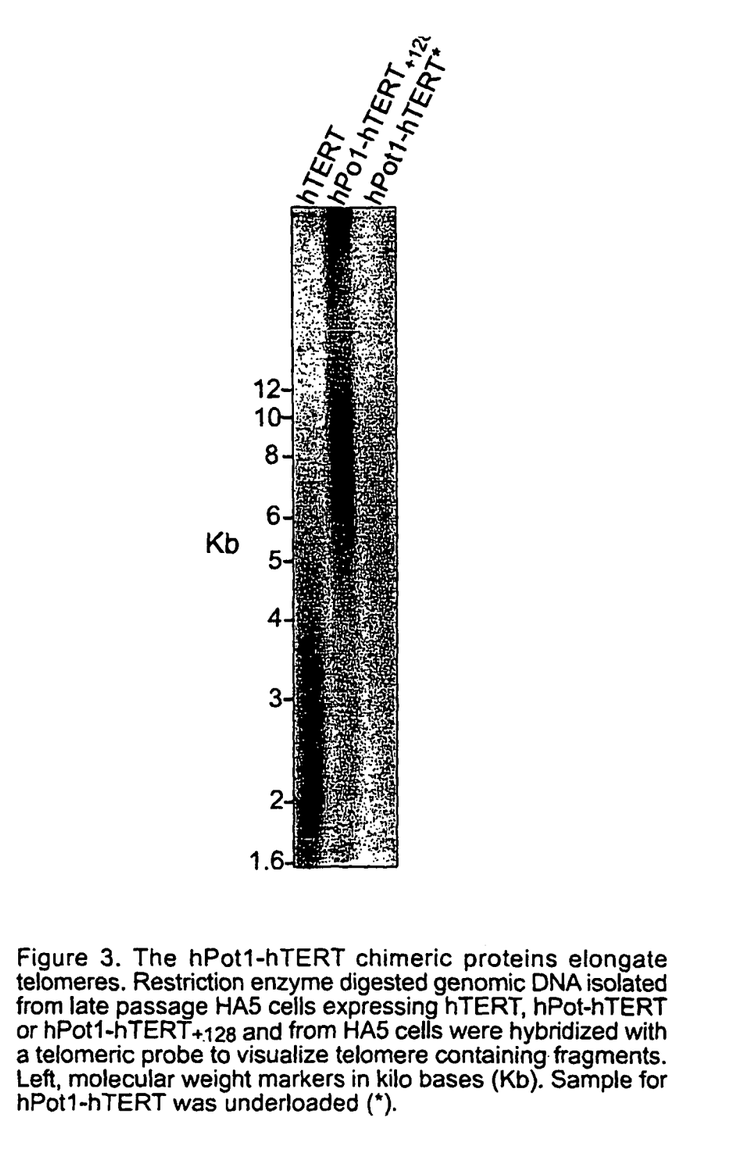
FIG. 3. The hPot1-hTERT chimeric proteins elongate telomeres. Restriction enzyme-digested genomic DNA isolated from late passage HA5 cells expressing hTERT, hPot-hTERT or hPot-hTERT$_{+128}$ were hybridized with a telomeric probe to visualize telomere containing fragments. Left, molecular weight markers in kilo bases (Kb). Sample for hPot-hTERT was underloaded (*).

Telomere Length Analysis (FIG. 3)

5 µg of genomic DNA isolated from late passage HA5 cells stably expressing flag-hTERT, flag-hPot1-flag-hTERT or flag-hPot1-flag-hTERT$_{+128}$, was digested with HinfI and RsaI restriction enzymes to release terminal restriction fragments containing telomeric DNA, Southern hybridized with a $^{32}$P-labeled telomeric $(C_3TA_2)_3$ oligonucleotide and exposed to a to phosphorimager screen (Molecular Dynamics), similar to methods previously described (Counter et al, EMBO J. 11:1921-1929 (1992)).

Results

Fusion of hPot1 to hTERT.

hPot1 has been shown to co-localize with the telomeric binding protein TRF2 by immunoflourescence analysis in vivo (Baumann et al, Mol. Ce. Biol. 22:8079-8087 (2002)), and associate with the G-rich strand of telomeric DNA in vitro (Baumann and Cech, Science 292:1171-1175 (2001)). Moreover, it has been shown that hPot1 co-immunoprecipitates specifically with telomeric DNA upon chemical crosslinking, indicating that hPot1 is a bona fide telomere binding protein. Because hPot1 binds single stranded telomeric DNA (Baumann and Cech, Science 292:1171-1175 (2001)) and because the budding yeast orthologue Cdc13p is known to cap the ends of the G-strand of telomeres (Nugent et al, Science 274:249-252 (1996)), the question presented was whether a fusion of hPot1 to the hTERT catalytic subunit of human telomerase (Meyerson et al, Cell 90:785-795 (1997)) might direct telomerase more often to telomeres, thereby greatly elongating telomeric DNA. To this end, a novel cDNA was created that encoded FLAG-epitope tagged hPot1 fused in frame FLAG-epitope tagged hTERT, termed hPot1-hTERT.

hPot1-hTERT is Expressed in Human Cells and Retains Telomerase Catalytic Activity.

To ascertain if, as predicted, hTERT targeted to telomeres by hPot1 results in telomere elongation, the cell strain HA5 was stably infected with retroviruses derived from constructs encoding the fusion protein or, as controls, hTERT or an empty vector. HA5 are a human embryonic kidney cell strain transformed with the early region of SV40 (Stewart and Bacchetti, Virology 180:49-57 (1991)). Since these cells lack telomerase activity, they lose telomeric DNA each cell division until a critically short length is reached, which leads to genomic instability and cell death (Counter et al, EMBO J. 11:1921-1929 (1992)) and hence can be used to monitor the ability of telomerase to function in vivo.

A protein of the predicted combined molecular weight of hTERT and hPot1 is specifically detected by immunoblotting with an antibody directed against the FLAG epitope engineered in the hPot1-hTERT fusion protein in cells infected with the retrovirus encoding hPot1-hTERT (FIG. 2A), indicating that the fusion protein is indeed expressed. As controls, immunoblot analysis confirmed the expression of hTERT or no transgene in the two control cultures (FIG. 2A).

Ectopic expression of hTERT is known to restore telomerase activity in HA5 cells, which normally lack hTERT (but express the hTR RNA subunit) (Meyerson et al, Cell 90:785-795 (1997)). Indeed, extracts isolated from both hTERT and hPot1-hTERT expressing cells, but not vector control cells, supported the elongation of a telomeric primer in vitro by the addition of telomeric repeats, which when PCR-amplified and resolved form a ladder indicative of telomerase catalytic activity (FIG. 2B). Thus, fusion of hPot1 to hTERT did not disrupt the catalytic activity of hTERT, arguing that the fusion protein is functional.

hPot1 Recruitment of hTERT to Telomeres Causes Dramatic Telomere Elongation.

Having ascertained that HA5 cells express the hPot1-hTERT fusion protein, the question presented was whether hTERT was better able to elongate telomeres when fused to hPot1. DNA was therefore isolated from late passage HA5 cells expressing hPot1-hTERT, or as a control hTERT, and digested with restriction enzyme HinF1 and RsaI to liberate telomere containing fragments, which when resolved on agarose gels were detected by Southern hybridization with a telomere specific probe. It was found, as previously reported (Counter et al, Proc. Natl. Acad. Sci. USA 95:14723-14728 (1998)), that HA5 cells expressing hTERT stabilized telomeres at a short length (FIG. 3). On the other hand, the same cell expressing the fusion protein exhibited greatly elongated telomeres, reaching telomere lengths at least three times larger than hTERT control cells (FIG. 3). Thus, the hPot1-hTERT fusion protein is far superior at elongating telomeres compared to the wild-type hTERT protein.

The hPot1-hTERT Fusion Protein Immortalizes Human Cells.

To determine if the fusion protein had any adverse affects on cell immortalization, the lifespan was monitored of HA5 cells expressing hPot1-hTERT or as controls, hTERT or no protein (vector). It was found, as expected, that vector control HA5 cells were mortal (FIG. 4), owing to the fact that telomere shortening was not arrested (Counter et al., EMBO J. 11:1921-1929 (1992)). On the other hand, cells expressing hTERT continued to proliferate well beyond the point when vector control cells perished at crisis (FIG. 4) due to the arrest of telomere shortening (FIG. 3). Importantly, cells expressing hPot1-hTERT grew similarly to hTERT-expressing cells, indicating that the fusion protein was not lethal and that it generated functional (but long) telomeres (FIG. 4). hPot1 fusion rescues the inability of a telomere-targeting mutant of hTERT to elongate telomeres.

A mutant of hTERT (hTERT$_{+128}$) was recently described with intact catalytic activity in vitro but defective in telomere elongation (Armbruster et al, Mol. Cell. Biol. 21:7775-7786 (2001)). Targeting this crippled enzyme to telomeres by fusion with the telomeric protein TRF2, which binds close but presumably not at the very ends of telomeres, partially rescued this defect. Cells expressing this fusion protein were immortal, but exhibited very short telomeres and a decreased proliferative rate (Armbruster et al, Mol. Cell. Biol. 23:3237-3246 (2003)). It was reasoned that since hPot1 may bind very close, if not to the ends of telomeres, fusion of hPot1 to hTERT$_{+128}$ may completely rescue this mutation. Therefore, hPot1-hTERT$_{+128}$ and as a control hTERT$_{+128}$ retroviral expression constructs were created from which retroviruses were generated. HA5 cells were then stably infected with these viruses and confirmed by immunoblot analysis to express either the hTERT$_{+128}$ or the hPot1-hTERT$_{+128}$ proteins (FIG. 2A). Extracts isolated from these two cell lines also showed equal levels of telomerase activity, indicating that the fusion did not disrupt the catalytic activity of hTERT$_{+128}$.

Control cultures grew as expected, with hTERT$_{+128}$-expressing cells entering crisis and dying with short telomeres (FIG. 4). However, cells expressing hPot1-hTERT$_{+128}$ proliferated indefinitely (FIG. 4) and exhibited a dramatic increase in telomere length (FIG. 3). Thus, targeting hTERT$_{+128}$ to telomeres by hPot1 not only rescued the inability of the crippled telomerase to replicate telomeres, but also greatly enhanced the ability of this hTERT protein to elongate this DNA. The data indicate that the hPot1-hTERT generates a remarkably active enzyme capable of elongating telomeres even when hTERT is critically mutated.

All documents cited above are hereby incorporated in their entirety by reference.

What is claimed is:

1. An isolated nucleic acid sequence encoding a chimeric molecule comprising a polypeptide having telomerase catalytic activity fused to a telomere binding polypeptide wherein said nucleic acid sequence comprises the nucleotide sequence set forth in SEQ ID NO:1.

2. An expression construct comprising said nucleic acid sequence according to claim 1 operably linked to a promoter.

3. A vector comprising the nucleic acid sequence according to claim 1.

4. The vector according to claim 3 wherein said vector is a viral vector.

5. The vector according to claim 4 wherein said viral vector is a retroviral vector, adeno-associated viral vector, lentiviral vector or adenoviral vector.

6. A liposome comprising the nucleic acid sequence according to claim 1.

7. A composition comprising the nucleic acid sequence according to claim 1 encapsulated in a polymer.

8. An isolated cell comprising the nucleic acid sequence according to claim 1.

9. The cell according to claim 8 wherein said cell is a stem or progenitor cell.

10. The cell according to claim 8 wherein said cell is an epithelial cell or a fibroblast.

11. The cell according to claim 8 wherein said cell is a muscle cell, nervous system cell, or keratinocyte.

12. The cell according to claim 8 wherein said cell is a human cell.

13. The cell according to claim 8 wherein said cell is immortal.

14. A method of producing a protein comprising culturing said cell according to claim 8 under conditions such that said nucleic acid sequence is expressed and said molecule is thereby produced.

* * * * *